US008206152B2

(12) United States Patent
Holzner et al.

(10) Patent No.: US 8,206,152 B2
(45) Date of Patent: Jun. 26, 2012

(54) METHOD CONCERNING THE MODELLING AND PRODUCTION OF A SET OF ARTIFICIAL TEETH

(75) Inventors: Stephan Holzner, Hohenschäftlarn (DE); Gerhard Weber, Pürgen (DE)

(73) Assignee: Institut Straumann AG, Basel (CH)

( * ) Notice: Subject to any disclaimer, the term of this patent is extended or adjusted under 35 U.S.C. 154(b) by 264 days.

(21) Appl. No.: 12/522,072

(22) PCT Filed: Jan. 3, 2008

(86) PCT No.: PCT/EP2008/000024
§ 371 (c)(1),
(2), (4) Date: Oct. 15, 2009

(87) PCT Pub. No.: WO2008/081003
PCT Pub. Date: Jul. 10, 2008

(65) Prior Publication Data
US 2010/0086899 A1    Apr. 8, 2010

(30) Foreign Application Priority Data

Jan. 3, 2007    (DE) .......................... 10 2007 001 045
Jan. 15, 2007   (DE) .......................... 10 2007 002 178

(51) Int. Cl.
| A61C 13/10 | (2006.01) |
| A61C 13/08 | (2006.01) |
| A61C 13/12 | (2006.01) |
| A61C 13/225 | (2006.01) |
| A61C 8/00 | (2006.01) |
| A61C 13/00 | (2006.01) |
| A61C 13/20 | (2006.01) |
| G06F 19/00 | (2011.01) |
| G06K 9/00 | (2006.01) |

(52) U.S. Cl. ..... 433/195; 433/171; 433/172; 433/199.1; 433/201.1; 433/203.1; 700/98; 700/118; 382/154; 264/17

(58) Field of Classification Search ............. 700/95–98, 700/117–120; 433/2, 3, 6, 24, 167, 171–175, 433/180–183, 199.1, 201.1, 202.1, 203.1, 433/213, 215, 218, 223, 191, 193–195; 382/128, 382/154; 264/16–20
See application file for complete search history.

(56) References Cited

U.S. PATENT DOCUMENTS 6,648,645 B1   11/2003   MacDougald
(Continued)

FOREIGN PATENT DOCUMENTS

CA   2371357 A1   9/2002
(Continued)

OTHER PUBLICATIONS

International Search Report and Written Opinion in corresponding PCT/EP2008/000024.
(Continued)

*Primary Examiner* — Crystal J Barnes-Bullock
(74) *Attorney, Agent, or Firm* — Rissman, Hendricks & Oliverio LLP

(57) ABSTRACT

Method for producing a base part of a set of artificial teeth, or a set of artificial teeth having a base part, comprising the step of forming the base part by a rapid prototyping process, e.g. 3D lithography and, in particular, 3D laser lithography. Furthermore, the invention relates to a method of establishing a data set representing the shape of a base part of a set of artificial teeth, wherein a gum area or a model thereof is scanned and/or a model of a base part is scanned and/or the shape of the base part is simulated on a computer.

24 Claims, 3 Drawing Sheets

U.S. PATENT DOCUMENTS

| | | | |
|---|---|---|---|
| 6,918,761 B2* | 7/2005 | Sachdeva et al. | 433/24 |
| 7,020,325 B2* | 3/2006 | Park | 382/154 |
| 7,077,646 B2* | 7/2006 | Hilliard | 433/6 |
| 7,153,135 B1 | 12/2006 | Thomas | |
| 7,347,688 B2* | 3/2008 | Kopelman et al. | 433/24 |
| 7,387,511 B2* | 6/2008 | Marshall | 433/3 |
| 7,476,100 B2* | 1/2009 | Kuo | 433/6 |
| 7,661,956 B2* | 2/2010 | Powell et al. | 433/172 |
| 7,699,610 B2* | 4/2010 | Childress | 433/167 |
| 7,899,221 B2* | 3/2011 | Weber et al. | 382/128 |
| 8,011,925 B2* | 9/2011 | Powell et al. | 433/172 |
| 8,043,091 B2* | 10/2011 | Schmitt | 433/196 |
| 8,047,846 B2* | 11/2011 | Wen | 433/213 |
| 8,060,236 B2* | 11/2011 | Hilliard | 700/160 |
| 2002/0064759 A1* | 5/2002 | Durbin et al. | 433/213 |
| 2003/0222366 A1 | 12/2003 | Stangel | |
| 2004/0219490 A1 | 11/2004 | Gartner | |
| 2006/0063135 A1* | 3/2006 | Mehl | 433/223 |
| 2009/0026643 A1* | 1/2009 | Wiest et al. | 264/16 |
| 2009/0220916 A1* | 9/2009 | Fisker et al. | 433/201.1 |
| 2009/0287332 A1* | 11/2009 | Adusumilli et al. | 700/98 |
| 2011/0281235 A1* | 11/2011 | Weissman | 433/173 |
| 2012/0065756 A1* | 3/2012 | Rubbert et al. | 700/98 |

FOREIGN PATENT DOCUMENTS

| | | |
|---|---|---|
| EP | 1 243 231 A | 9/2002 |
| EP | 1 444 965 A | 8/2004 |
| WO | WO 2008/005432 A | 1/2008 |

OTHER PUBLICATIONS

Jul. 16, 2009 International Preliminary Report on Patentability in corresponding PCT/EP2008/000024 (in German) and Aug. 13, 2009 English Translation of International Preliminary Report on Patentability.

* cited by examiner

METHOD CONCERNING THE MODELLING AND PRODUCTION OF A SET OF ARTIFICIAL TEETH

FIELD OF THE INVENTION

The invention relates to the production of sets of artificial teeth including a base part, and to the production of such a base part itself.

BACKGROUND

A set of artificial teeth is also referred to as "dentures". Such a set of artificial teeth includes a base part which is normally gum-coloured and in which or on which artificial teeth are provided. Such base parts must each be custom made for each individual patient. The base part is fitted onto a gum area in which teeth are missing. It can be provided for an upper jaw or for a lower jaw.

The sets of artificial teeth dealt with in the present connection are configured as removable sets of teeth. They are held on the gums e.g. by denture fixatives.

SUMMARY OF THE INVENTION

It is the object of the present invention to improve the production of a set of artificial teeth and/or of a base part thereof.

In accordance with one embodiment of the invention, a method is provided for producing a base part of a set of artificial teeth, or a set of artificial teeth having a base part, comprising the step of:
forming the base part by a computer-aided production process, such as a rapid prototyping process, e.g. 3D lithography and, in particular, 3D laser lithography, a computer-aided milling process or some other removing or applying computer-aided production process.

In accordance with another embodiment, a method is provided for establishing a data set representing the shape of a base part of a set of artificial teeth, or the shape of a set of artificial teeth including a base part, wherein
a) a gum area or a model thereof is scanned and/or
b) a model of a base part is scanned and/or
c) the shape of the base part is simulated on a computer.

In accordance with another embodiment, a machine-readable data carrier is provided comprising instructions which will cause a computer to execute a method as previously described.

In accordance with another embodiment, a computer is provided with a machine-readable data carrier as previously described.

According to the method for producing a (removable) set of artificial teeth, the base part is produced by a computer-aided production process, such as a rapid prototyping process. A rapid prototyping process is, quite generally, a primary forming method by means of which the workpiece is built (e.g. in layers) from shapeless or shape-neutral materials by utilizing physical and/or chemical effects. Such a rapid prototyping process can be e.g. the 3D lithography and, in particular, the 3D laser lithography. Other examples of rapid prototyping processes are stereolithography, selective laser sintering, laser generation, fused deposition modelling, laminated object modelling, 3D printing, contour crafting, multi-jet modelling or polyjet processes.

In the case of 3D laser lithography, e.g. a synthetic resin is locally heated by a laser or a chemical reaction is caused by the laser light irradiation so that the liquid material solidifies. What can also be used here is melting a material in powder form which will then harden in a fused form during cooling.

Computer-aided removing or applying production processes can be used as well. One example for a removing computer-aided process is computer-aided milling. In the case of applying computer-aided productions processes, layers of material, laminae or parts are applied one after the other so as to produce the workpiece.

The liquid or powdery material used in a rapid prototyping process or in some other applying process can have e.g. a gum-coloured or a tooth-coloured hue already prior to the forming step. If the (rapid prototyping) process is only used for producing the base part, the desired hue, i.e. especially a gum-coloured hue, can already be achieved by such colouring without any further follow-up treatment. In addition, the hue achieved can also be changed during the rapid prototyping process, e.g. from gum-coloured to tooth-coloured and/or from a first gum colour to one or a plurality of other gum colours and/or from one tooth colour to one or a plurality of other tooth colours.

On the other hand, it is also possible that a base part produced by a (rapid prototyping) process is fully or partly redyed so as to achieve a desired hue, in particular a gum-coloured hue, or shades of colour, colour gradients etc.

Furthermore, a method will be of advantage in the case of which also teeth of the set of artificial teeth are produced by the (rapid prototyping) process. These teeth can be formed integrally with the base part (but possibly with at least two different colours according to an advantageous embodiment) or they can also be produced separately of said base part. These teeth produced by the (rapid prototyping) process can have applied thereto one or a plurality of colour coats and/or one or a plurality of other layers increasing e.g. the wear resistance. Colour coats can also be applied to the base part.

Since the demands on the material of the base part and on the material of the artificial teeth are normally markedly different and since in particular the teeth must fulfil very high requirements as regards breaking and wear resistance, it will also be of advantage when prefabricated artificial teeth are provided for the set of artificial teeth. These prefabricated teeth can be connected to the base part in an appropriate manner. They can, for example, also be inserted. For the purpose of connection, an adhesive can be provided and/or mechanical connection means, such as a screw, a thread, a pin, a bayonet joint or other mechanical connection means.

Possible connection means on the base part for fastening the artificial teeth or tooth veneers can preferably be formed integrally with the base part. It will be of advantage to produce them by one and the same rapid prototyping process which is also used for producing the base part itself.

According to an advantageous embodiment, the shape of the base part is modelled by a computer. For this purpose, e.g. the shape of the gum area to which the set of artificial teeth is to be fitted can be scanned directly, or a model of this gum area can be scanned. The shape of the gum area can then be used for modelling the shape of the base part.

On the other hand, it is also possible that the shape of the base part is determined through a model of the base part. In this case, e.g. a model of the base part is built onto a model of the gum area (e.g. with wax) and is then recorded e.g. by scanning so that a data set will be provided, which represents the shape of the model of the base part.

In this connection, it will especially be advantageous to use a method in the case of which the inner shape of the base part is determined on the basis of the shape of the gum area (or of a model thereof) and the outer shape is either simulated by a computer or determined by scanning a model of a base part.

The shape of the base part and/or the shape of the set of artificial teeth and/or one or more data sets corresponding to these shapes, are permanently archived according to an advantageous embodiment. It will thus e.g. be possible to produce later on, when the set of artificial teeth is worn-out, a new, but identical set of artificial teeth. This can be done e.g. on demand of a patient (or of the patient's dentist). The demand can e.g. be received by Internet, i.e. the new set of artificial teeth can be ordered via the Internet.

The invention also relates to a method of establishing a data set representing the shape of a base part of a set of artificial teeth.

In this respect, each of the above-mentioned method steps can be used. For example, a gum area and/or a model thereof can be scanned. Furthermore, a model of a base part can be scanned or the shape of the base part can be simulated on a computer.

A data set for producing a base part can either be transmitted locally to a rapid prototyping device or to some other computer-aided production device or it can be sent through remote data transmission to a production centre, which will then use said data set for executing a rapid prototyping process or some other computer-aided production process so as to produce the base part.

In addition, machine-readable data carriers and computers for executing the methods referred to hereinbefore or hereinbelow are provided.

BRIEF DESCRIPTION OF THE DRAWINGS

Preferred embodiments of the invention will be explained making reference to the figures enclosed, in which.

DETAILED DESCRIPTION

Figure 1:
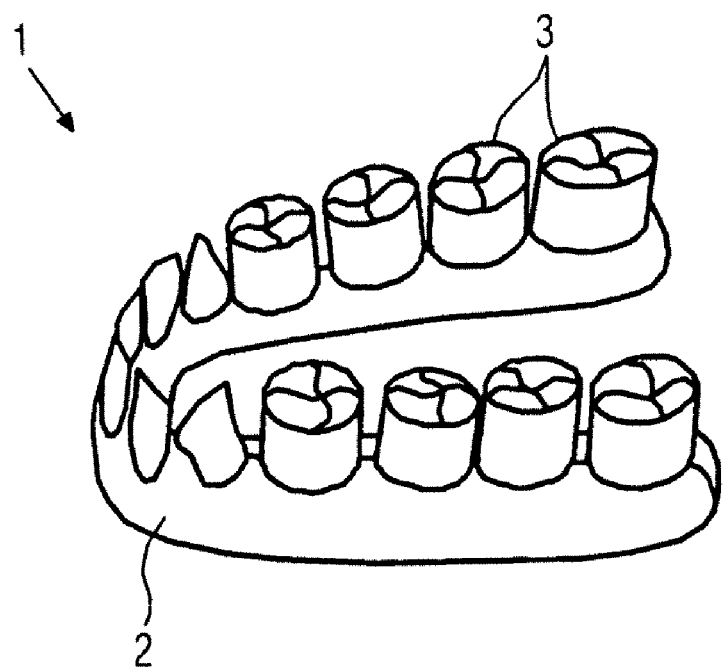
FIG. 1 shows a set of artificial teeth.

FIG. 1 shows a set of artificial teeth 1 comprising a base part 2 and artificial teeth 3. The base part 2 should preferably be gum-coloured and the teeth 3 should preferably be tooth-coloured, i.e. they should essentially be held in a shade of white.

Such a set of artificial teeth can be provided for the upper jaw or the lower jaw. Whereas FIG. 1 shows a full denture, in the case of which all the teeth of one jaw are replaced, the denture provided may also only be a partial denture, which covers only part of the jaw and replaces thus only part of the teeth.

The teeth 3 can be formed integrally with the base part 2. They may, however, also be implemented such that they are not integral with the base part 2. The base part 2 itself is preferably a one-piece component, it may, however, also be implemented as a two-, three- or multi-piece component.

Figure 2A:
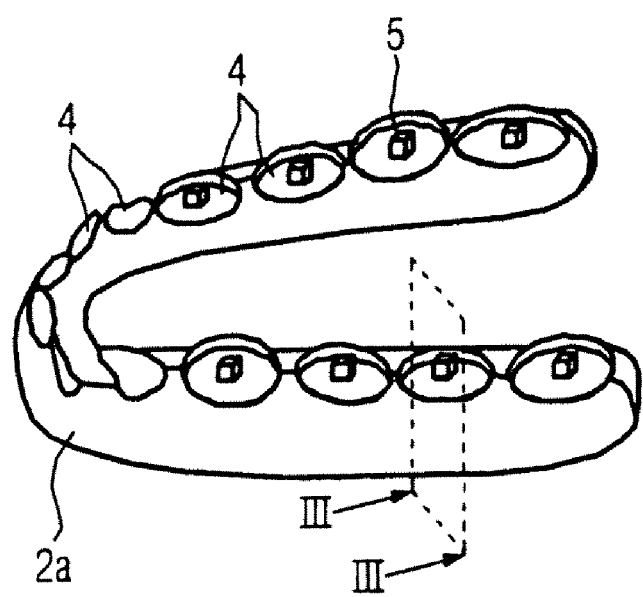
FIG. 2 shows various variants of base parts.

FIG. 2a shows a base part 2a having provided therein openings or recesses 4 into which the artificial teeth are inserted. Furthermore, a fastening means 5 is shown in the area of the molars, said fastening means 5 being preferably formed integrally with the base part 2a. More detailed explanations to the fastening means are contained in the description relating to FIG. 3.

Figure 2B:
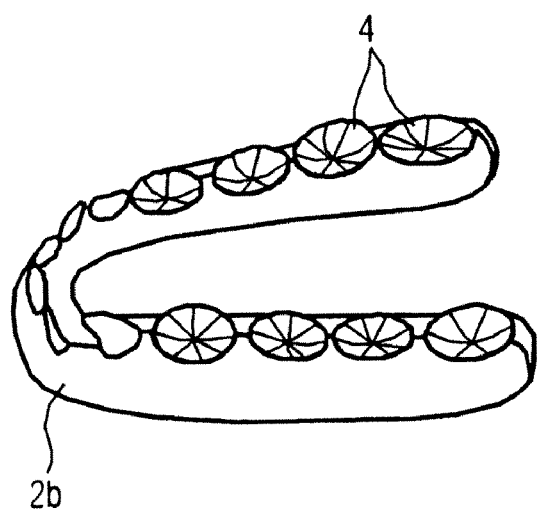

In FIG. 2b a base part 2b is shown, in which recesses 4 for receiving therein the respective artificial teeth are provided. Special additional fastening means 5 are here not provided.

In FIG. 3 various sections are shown, said sections being made at the location indicated in FIG. 2a under III. FIG. 3a shows a sectional view of a base part 2c whose lower surface (inner side) is formed irregularly depending on the gum area to which the set of artificial teeth is to be fitted. The lateral outer surface is designed according to aesthetical and stability aspects. The upper side of the base part 2c has arranged thereon an artificial tooth 3c whose lower end is provided with a recess into which the fastening means 5 can be inserted. The artificial tooth 3c can e.g. be glued on. By means of the cubic fastening means 5, a rotational displacement of the artificial tooth 3 can be prevented effectively and the position of the artificial tooth 3c can be defined precisely, when said tooth is glued on.

Figure 3A:
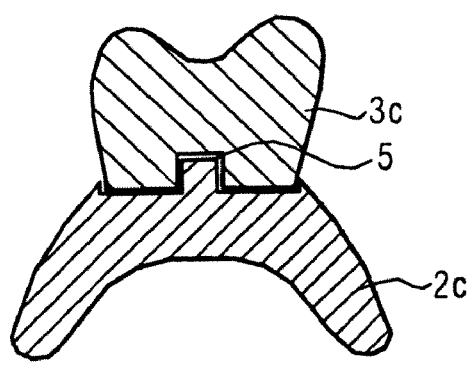
FIG. 3 shows various sectional views of sets of artificial teeth.
Figure 3B:
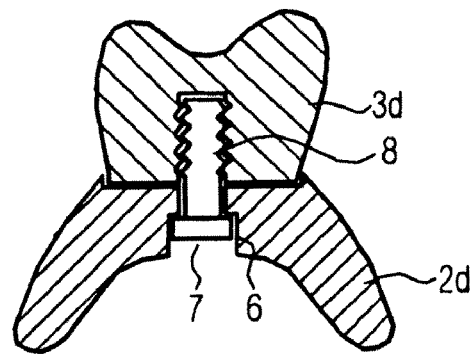

In FIG. 3b an alternative embodiment is shown, in the case of which an artificial tooth 3d is provided with a female thread 8 which is engaged by a screw 7. The base part 2d has provided therein a recess 6 accommodating the head of the screw 7 in the fixed condition. The opening 6 can also be filled, when the screw 7 has been inserted and tightened.

Figure 3C:
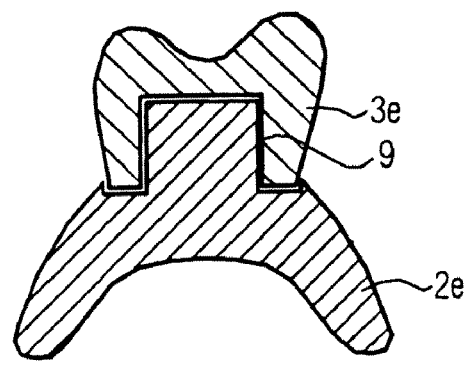

FIG. 3c shows a variant in the case of which a base 9 is provided on the upper surface of the base part 2e, said base 9 having only attached thereto a tooth veneer 3e. This artificial tooth veneer 3e exhibits an appropriate hue for teeth and guarantees high wear resistance. Materials that can be used here are e.g. porcelain materials, ceramic materials or the like. The base used for a tooth veneer has a volume of at least 30%, 50%, 70%, 80% or 90% of the volume occupied and/or enclosed by the veneer.

Figure 3D:
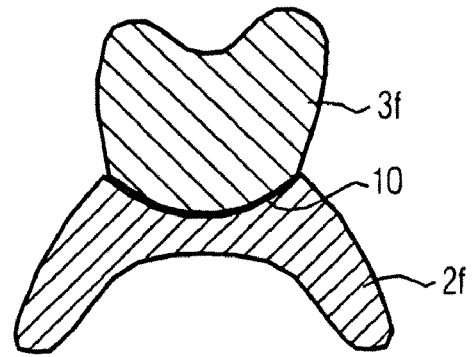

FIG. 3d shows a further variant according to which a round recess 10, into which an artificial tooth 3f can be glued, is provided on the upper side of the base part 2f.

The variant according to FIG. 3d corresponds approximately to the base part shape according to FIG. 2b.

The respective shapes of the recess 4 and/or of the fastening means 5, 6, 9, 10 can be determined on the basis of data that are known in advance. In the case of prefabricated teeth, the shape of the tooth is known so that the required shape of the base part is known as well. This shape is preferably stored in an electronic library or file or database and can be retrieved for modelling the base part.

The shape required for the respective teeth can be incorporated in a data set describing the base part; this data set can have been created (e.g.) by scanning a model or by modelling a base part on the computer.

Figure 4:
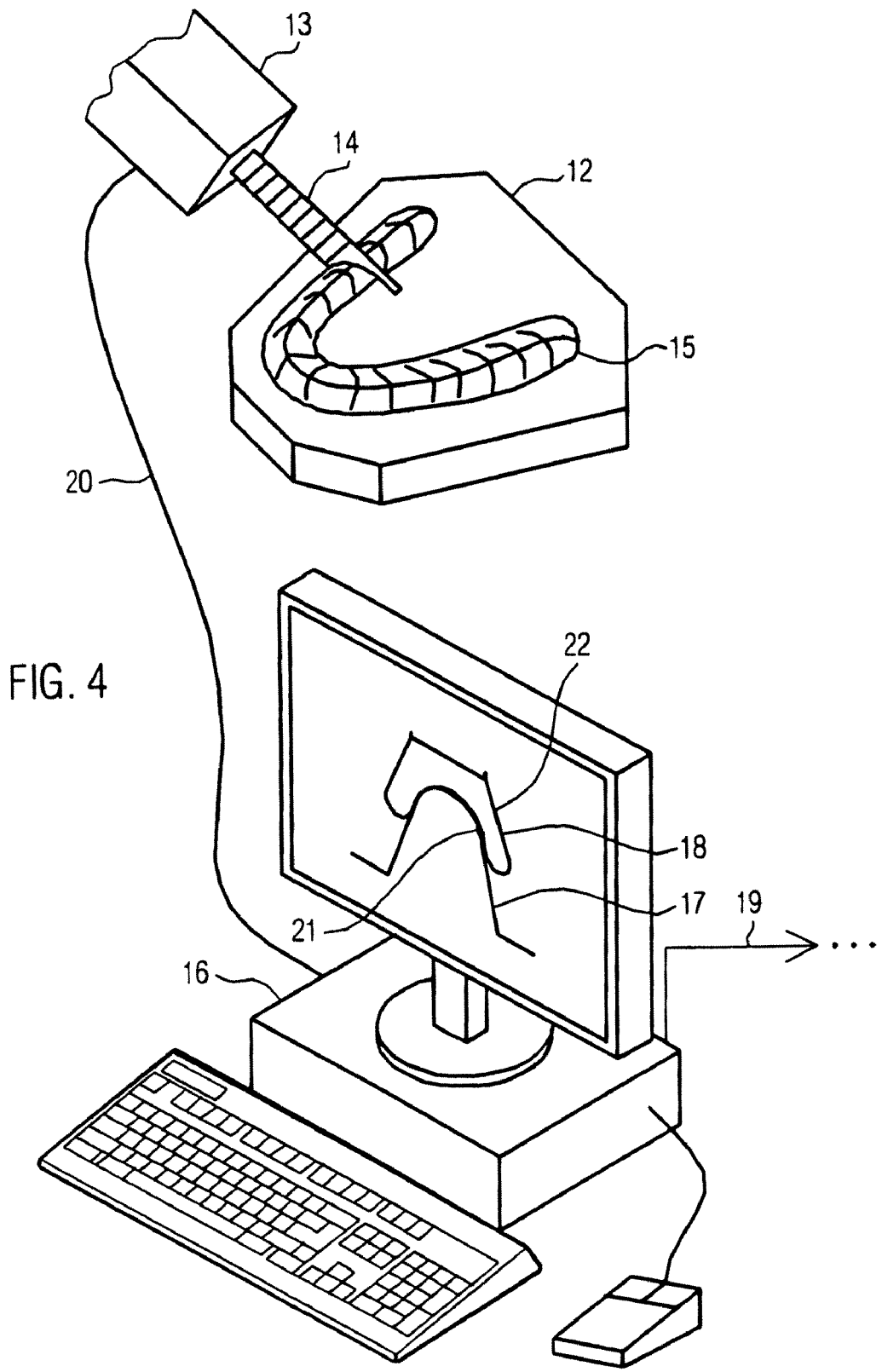
FIG. 4 shows a schematic representation of components for executing methods or method steps.

FIG. 4 shows a scanner 13 (which is here, by way of example, an optical scanner) that can be used for scanning a shape of a model or of a gum area. In FIG. 4, a model 12 is provided, which has on the upper side thereof a region 15 representative of the shape of a gum area. This region can be scanned with the scanner 13 (cf. exemplarily the light beam 14). The data of the scanner 13 can be transmitted to a computer 16. For this purpose, a data connection 20 (cable-bound or wireless data connection) is provided. On the monitor of the computer 16 a data set 17 is shown, which represents the shape of the gum region 15. Furthermore, a data set 18 which represents the shape of a base part is shown on the monitor. Taking as a basis the data set 17, this data set 18 can be created on the computer by simulation. The inner or lower side 21 of the data set 18 (i.e. the region which will face the gum area or come into contact therewith) is preferably formed on the basis of the acquired data 17. This will lead to an optimum fitting accuracy. The thickness of the base part and, consequently, its stability is determined by the outer side 22. In the case of the model 12, a base part can, however, also be modelled onto the region 15. Said model 12 can be scanned by the scanner 13 and the shape for the outer side 18 of the base part can be developed in this way. Such data acquired by scanning can be reworked by means of a computer (e.g. modification of the inner or outer side, insertion of shaped elements for artificial teeth, such as recesses or fastening means, etc.).

A particularly advantageous method is so conceived that the region 15 is first scanned for acquiring the data for the inner side 21 of the base part and that the outer side 22 is then either simulated on the computer 16 or a model is modelled onto the region 15 and scanned so as to obtain the data for the outer side 22. Also combinations of these last two method variants are possible by scanning e.g. a model of the base part, said model being, however, subsequently reworked on the computer. Such reworking can especially be used for adding e.g. the fastening means for the artificial teeth.

A data set 18, which represents the shape of a base part, can be transmitted with data transmission means 19, e.g. an Internet connection, through remote data transmission to a production centre for base parts. The data set 18 may, however, also be transmitted locally to a rapid prototyping system which will then produce an appropriate base part.

The data describing the parts produced (base part, teeth, set of artificial teeth, etc.), or other data that can be used for producing said parts, can be archived for a long time (one, two, three, four, five or more years). This allows the use of said data for the production of a second or further set of artificial teeth. The archiving does preferably not take place on the computer 16, but on a mass data storage device, such as a recordable CD, DVD, a magnetic tape, a data store or the like.

A base part of the type shown in FIG. 2b can have applied thereto one or a plurality of colour coats. Desired colour gradients, hues and shades of colour can be accomplished in this way, as can e.g. be done by a dental technician.

Colour coats or layers increasing the wear resistance can also be applied to the artificial teeth or the base (cf. FIG. 3c) by a dental technician.

The invention claimed is:

1. A method of producing a base part of a set of artificial teeth, or a set of artificial teeth having a base part, wherein in the base part or on the base part the artificial teeth are provided, wherein the base part is individual for each individual patient and wherein the base part is fitted onto a gum area in which teeth are missing, comprising the steps of:
    recording the shape of a gum area, using the recorded shape of the gum area for fully or partly determining the interior shape of the base part, modeling a model of the base part onto a model of the gum area, recording the shape of the model of the base part and using the recorded shape of the model of the base part for fully or partly determining the outer shape of the base part; or
    recording the shape of a model of a gum area, using the recorded shape of the model of the gum area for fully or partly determining the interior shape of the base part, modeling a model of the base part onto the model of the gum area, recording the shape of the model of the base part and using the recorded shape of the model of the base part for fully or partly determining the outer shape of the base part;
    the method further comprising the steps of:
    forming the base part with fastening means for artificial teeth, said fastening means being formed integrally with the base part, the lower end of an artificial tooth being provided with a recess into which a fastening means can be inserted; and
    forming the base part by a computer-aided production process.

2. A method according to claim 1, wherein the material used for forming the base part has, already prior to said forming, a gum-coloured or a tooth-coloured hue.

3. A method according to claim 1, wherein the base part is dyed, after or during the forming step.

4. A method according to claim 1, wherein also the teeth of the set of artificial teeth are produced by the computer-aided production process, said teeth being produced such that they are integral with the base part.

5. A method according to claim 1, wherein prefabricated artificial teeth are inserted in the base part and/or connected thereto.

6. A method according to claim 1, wherein the base part is formed with fastening means for or tooth veneers, said fastening means being formed integrally with the base part.

7. A method according to claim 1, wherein the shape of the base part is fully or partly modelled by a computer.

8. A method according to claim 7, wherein for modelling the shape of the base part a data set is used, which represents the shape of the gum area of a patient.

9. A method according to claim 8, wherein the data set is obtained by scanning a model of the gum area or by scanning the gum area of a patient.

10. A method according to claim 1, wherein the shape of the base part or the shape of the outer side of the base part is determined fully or partly by a model of the base part.

11. A method according to claim 10, wherein a data set is established, which represents fully or partly the shape of the model of the base part.

12. A method according to claim 10, wherein the data set is established by scanning the model of the base part.

13. A method according to claim 1, wherein a second forming of the base part and/or of the artificial teeth is by a computer-aided production process.

14. A method according to claim 13, wherein the second forming computer-aided production process is a rapid prototyping process, a computer-aided milling process or some other removing or applying computer-aided production process.

15. A method according to claim 14, wherein the second forming computer-aided production process is a 3D lithography or a 3D laser lithography process.

16. A method according to claim 14, wherein said second forming is carried out on demand of the patient and/or of a dentist and/or executed more than one year after the first forming.

17. A method according to claim 1, wherein a data set, which fully or partly represents the shape of the model of the base part, is archived for at least one year.

18. A method according to claim 1, wherein the computer-aided production process is a rapid prototyping process, a computer-aided milling process or some other removing or applying computer-aided production process.

19. A method according to claim 1, wherein the computer-aided production process is 3D lithography.

20. A method according to claim 19, wherein the computer-aided production process is 3D laser lithography.

21. A method according to claim 1, wherein the prefabricated artificial teeth are connected to the base part with an adhesive or mechanical connection means.

22. A method according to claim 1, wherein the prefabricated artificial teeth are connected to the base part with a screw, a thread, a pin, or a bayonet joint.

23. A method of establishing a data set representing the shape of a base part of a set of artificial teeth, or the shape of a set of artificial teeth including a base part, wherein in the base part or on the base part the artificial teeth are provided, wherein the base part is individual for each individual patient and wherein the base part is fitted onto a gum area in which teeth are missing, wherein
a) a gum area or a model thereof is scanned, the method further comprising the steps of: fully or partly determining the interior shape of the base part by using the scanned gum area or the scanned model thereof;

modeling a model of the base part onto the model of the gum area, recording the shape of the model of the base part and using the recorded shape of the model of the base part for fully or partly determining the outer shape of the base part; the method further comprising the steps of: forming the base part with fastening means for artificial teeth, said fastening means being formed integrally with the base part, the lower end of an artificial tooth being provided with a recess into which a fastening means can be inserted; and/or
b) a model of a base part is scanned and/or
c) the shape of the base part is simulated on a computer.

24. A method according to claim 23, wherein the data set for producing a base part is transmitted locally or through remote data transmission.

* * * * *

UNITED STATES PATENT AND TRADEMARK OFFICE
CERTIFICATE OF CORRECTION

PATENT NO. : 8,206,152 B2
APPLICATION NO. : 12/522072
DATED : June 26, 2012
INVENTOR(S) : Holzner et al.

It is certified that error appears in the above-identified patent and that said Letters Patent is hereby corrected as shown below:

At Col. 6, line 14:

delete "or"

Signed and Sealed this
Fourteenth Day of August, 2012

David J. Kappos
*Director of the United States Patent and Trademark Office*